May 16, 1972 R. B. TAYLOR, JR Plant Pat. 3,168
HOLLY BUSH
Filed March 20, 1970
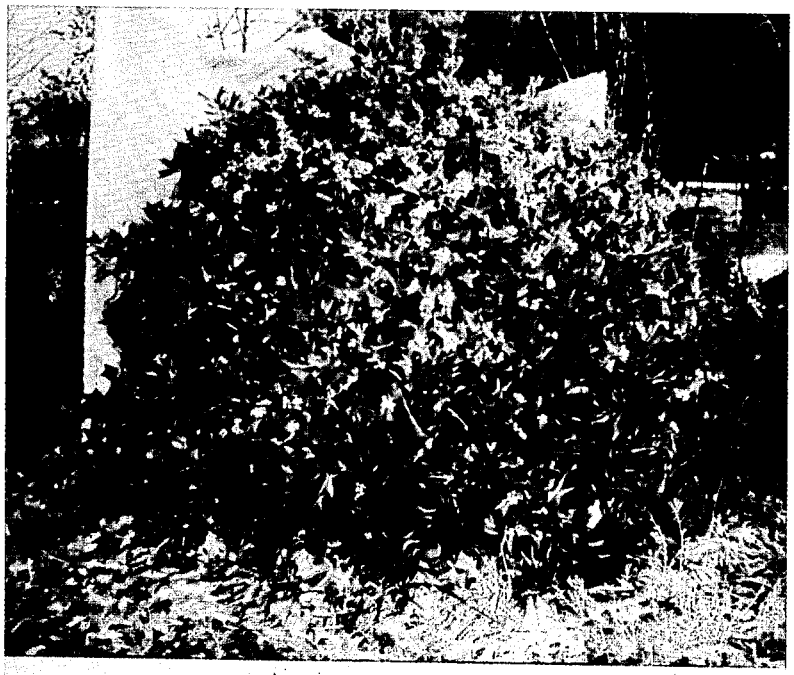
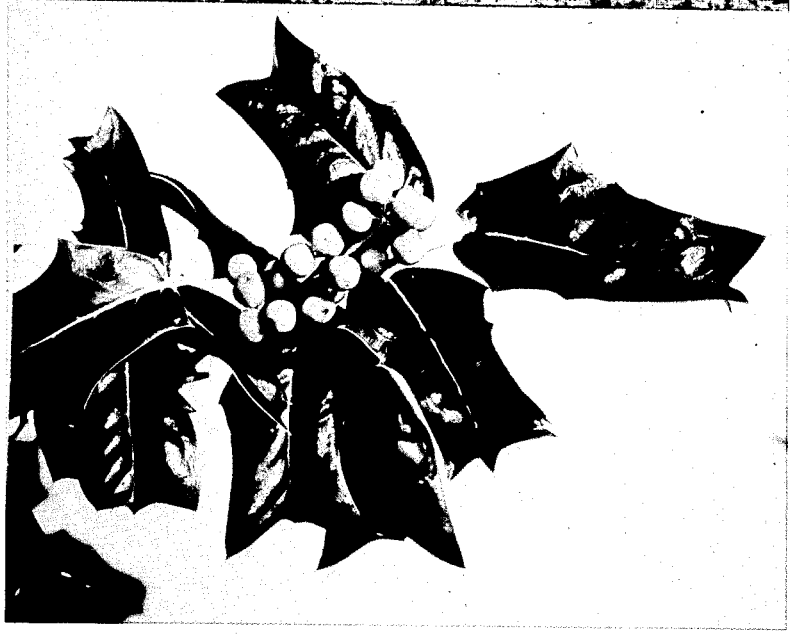
INVENTOR.
ROWELL B. TAYLOR,
By Edmond F. Shanahan
ATTORNEY.

United States Patent Office

Plant Pat. 3,168
Patented May 16, 1972

3,168
HOLLY BUSH

Rowell B. Taylor, Jr., Greer, S.C., assignor to Monrovia Nursery Company, Azusa, Calif.

Filed Mar. 20, 1970, Ser. No. 21,556
Int. Cl. A01h *5/00*
U.S. Cl. Plt.—65 1 Claim The present discovery relates to a new and distinct variety of ornamental plant of the Ilex genus, *cornuta* species, characterized as to novelty in its dwarf size and compact growth, its production of an abundance of berries, and its generally compact and decorative appearance suitable for elegant landscape gardening.

The new variety was discovered by me late in 1935, growing as a chance seedling in a bed of *Ilex cornuta* seedlings, an unpatented variety, that was being cultivated by me on my property located in the city of Greer, county of Greenville, state of South Carolina.

The plant was selected by me because I observed its distinctive and unique combination of very slow and compact growth, with high production of berries.

The plant has been asexually reproduced by me by means of cutting. Only a few cuttings have been taken from the original plant and all subsequent propagation has been from the plants grown from these cuttings. All descendants have shown the same characteristics as the original plant, indicating that the new variety has become well established. The plant does not produce true from seed.

The new variety does not resemble its presumed seed parent, which is normally an upright growing plant, either in its habit of growth or in the shape of its foliage. The original plant of the new variety after thirty-five (35) years of growth has only reached a height of about forty-eight (48) inches with a spread of about sixty (60) inches. No pruning has been practiced on this plant to cause it to develop this form.

A plant of the new variety, and a branch with berries, cut therefrom, are shown in full color in the accompanying illustration.

A detailed description of the new variety follows, and to falicitate identification of the important colors, the color terminology adopted by the British Horticultural Color Charts has been followed.

*The plant*

Parentage: Chance seedling.
*Seed parent.*—Unknown variety of *I. cornuta.*
*Pollen parent.*—Unknown.

General characteristics: The plant is dwarf in size, and is an upright tightly compact bush being only slightly taller than it is wide. The top being somewhat rounded. The plant is well clothed with foliage from ground level to the top.

Branches: The plant is densely branched from just above the ground level, with the main branches being somewhat ascending and the branchlets arching and spreading. The plant has no central leader or trunk and attains its shape from its dense branching habit.

Leaves: The leaves are thick (coriaceous), glossy, broad at the base, being 2 to 3½″ wide, tapering to 1⅝ to 2½″ at the apex. Total length of leaves is from 3 to 3⅞″ long. Petiole ¼″, grooved. Base of leaf is more or less truncated. Usual form of the *Ilex cornuta* leaf is rectangular.

Veins: On upperside of the leaf veins are recessed and are slightly raised underneath. Light green above, darker green underneath. Midrib prominent underneath.

Spines: Usually 7, but occasionally 6.

Color: On top of leaf 0001060/2, Ivy green, underside of leaf 0960/2, Spinach green.

Flowers: Characteristic of species (female).

Fruit: A flattened globe in shape varying from ½ to 9/16″ in width and from ⅜ to 7/16″ thick. Plant is very precocious, often producing fruit on cuttings only one (1) year old. Mature plants will produce a heavy crop of fruit. Color of the mature fruit 822, Cardinal Red.

I claim:

1. A new and distinct variety of *Ilex cornuta* plant substantially as shown and described, characterized by its dwarf size, its slow growth habit, its arching spreading branches with the absence of any central leader or trunk forming a tightly compact bush.

No references cited.

ROBERT E. BAGWILL, Primary Examiner